US00PP17514P3

(12) United States Plant Patent
Matsui

(10) Patent No.: US PP17,514 P3
(45) Date of Patent: Mar. 20, 2007

(54) ZOYSIAGRASS PLANT 'TM9'

(50) Latin Name: *Zoysia matrella Merr.*
Varietal Denomination: TM9

(75) Inventor: Kunio Matsui, Nishikamo-gun (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 162 days.

(21) Appl. No.: 10/936,495

(22) Filed: Sep. 9, 2004

(65) Prior Publication Data

US 2005/0114973 P1 May 26, 2005

(30) Foreign Application Priority Data

Nov. 21, 2003 (JP) ..... 16314

(51) Int. Cl.
*A01H 5/00* (2006.01)

(52) U.S. Cl. ..... Plt./390

(58) Field of Classification Search ..... Plt./390
See application file for complete search history.

*Primary Examiner*—Kent Bell
*Assistant Examiner*—Annette H Para
(74) *Attorney, Agent, or Firm*—Oblon, Spivak, McClelland, Maier & Neustadt, P.C.

(57) ABSTRACT

The present cultivar TM9 (*Zoysia matrella* Merr.) advantageously has a growing rate of in terms of plant height less than half as compared with existing cultivars and requires mowing every 20 to 40 days during the summer so as to be maintained in fair condition and allows the amount of fertilizer to be reduced to almost less than half.

5 Drawing Sheets

Latin name of the genus and species of the plant claimed: The present invention relates to the species *Zoysia matrella* Merr.

Variety denomination: 'TM9'.

BACKGROUND OF THE INVENTION

Field of Invention

The present invention relates to a new and distinct perennial variety of Zoysiagrass asexually reproduced and selected.

SUMMARY OF THE INVENTION

The present invention relates to a new and distinct Zoysiagrass cultivar (*Zoysia matrella* Merr.) named 'TM9'.

Zoysiagrass is a popular lawn grass which has been widely used as greening turf. The turf thereof, however, should be mown every 7 to 10 days during the summer so as to be maintained in beautiful condition. Since the newly developed TM9 advantageously has a growing rate in terms of plant height less than half as compared with conventional cultivars, moving is required every 20 to 40 days during the summer to maintain fair condition and the amount of fertilizer can be reduced to almost less than half. Therefore, labors and cost necessary for maintenance of the turf as well as clipping from lawn-mowing can be reduced. Furthermore, the cultivar can be readily grown in a place where a lawnmower cannot be conveniently used, such as on a rooftop of a building.

In addition, it is expected that prevalence of TM9 facilitates greening of the rooftop and schoolyard and leads to alleviation of heat island phenomenon and reduction of the amount of $CO_2$.

For purposes of registration under the "International Convention for the Protection of New Varieties of Plants"

(generally known by its French acronym as the UPOV Convention) and noting sections 1612 of the Manual of Patent Examining Procedure, it is proposed that the new variety of Zoysiagrass of the present invention be named 'TM9'.

BRIEF DESCRIPTIONS OF THE ILLUSTRATIONS

Figure 1:
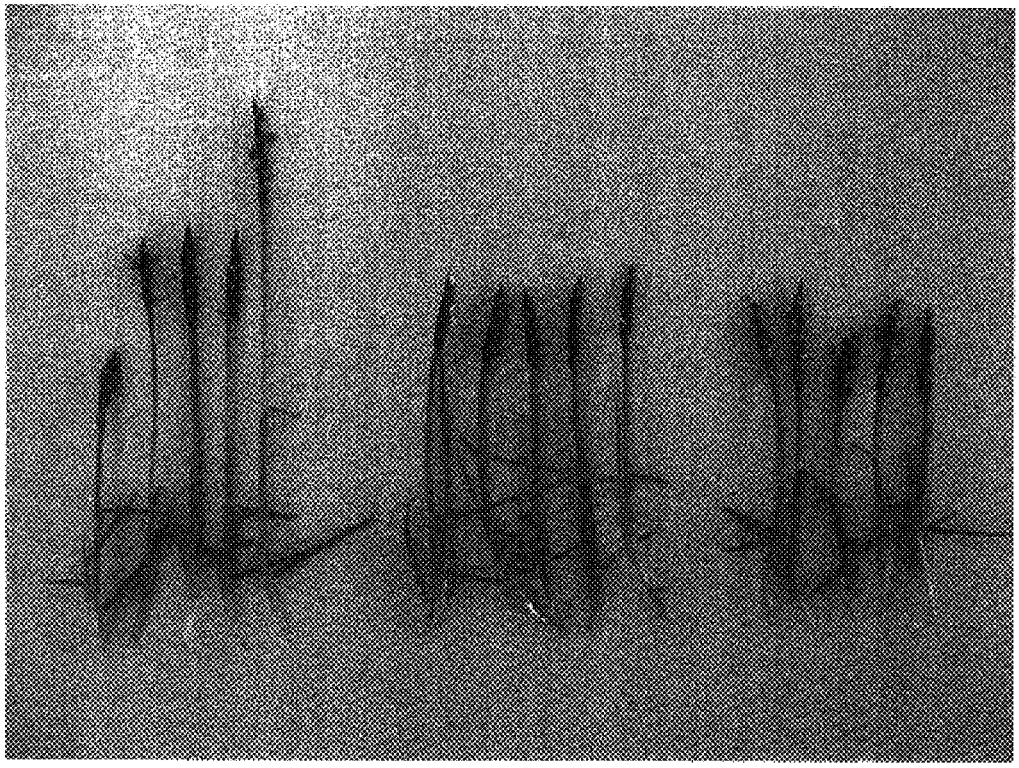

FIG. 1 is a set of photographs comparing spikestems of control cultivars and the present cultivar (TM9) (Left: Emerald; Middle: Winter Field; Right: TM9). Photographed on Jul. 15, 2003 in Hishikamo-gun, Aichi, Japan.

Figure 2:
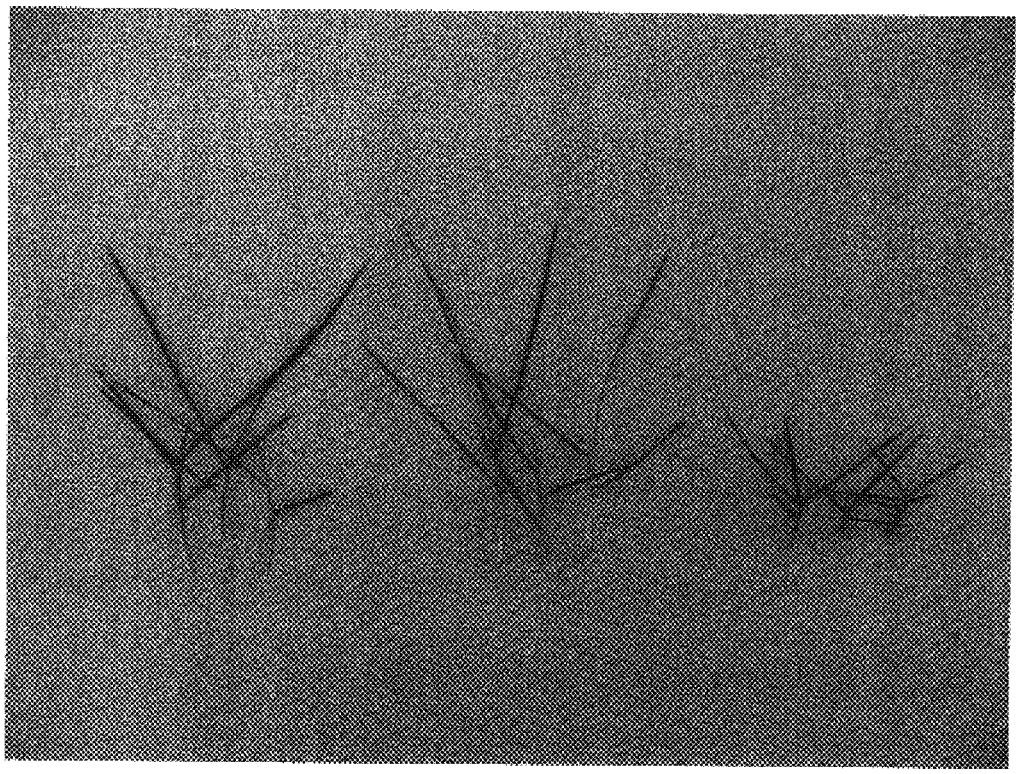

FIG. 2 is a set of photographs comparing leaf blades of control cultivars and the present cultivar (TM9) (Left: Emerald; Middle: Winter Field; Right: TM9). Photographed on Jul. 15, 2003 in Nishikamo-gun, Aichi, Japan.

Figure 3:
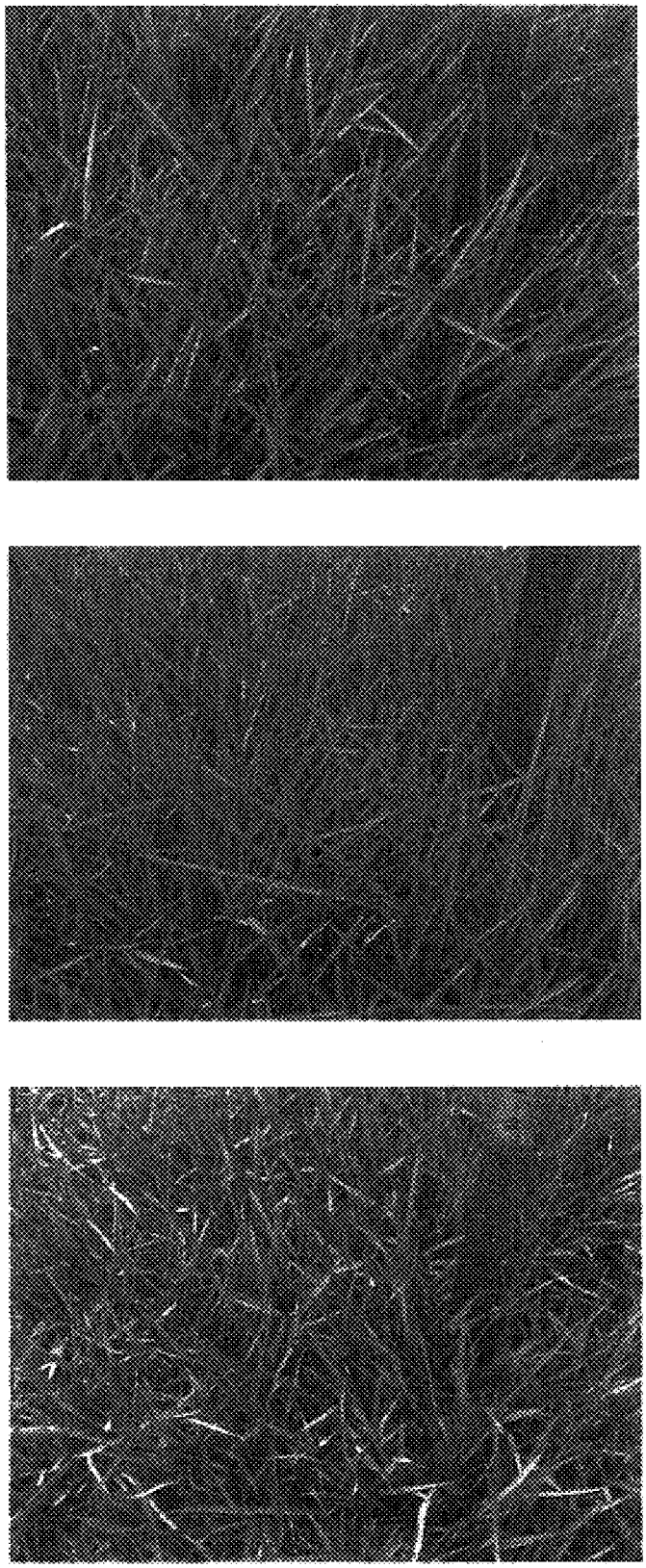

FIG. 3 is a set of photographs comparing grass shapes of control cultivars and the present cultivar (TM9) (Upper: Emerald; Middle: Winter Field; Lower: TM9). Photographed on Jul. 15, 2003 in Nishikamo-gun, Aichi, Japan.

Figure 4:
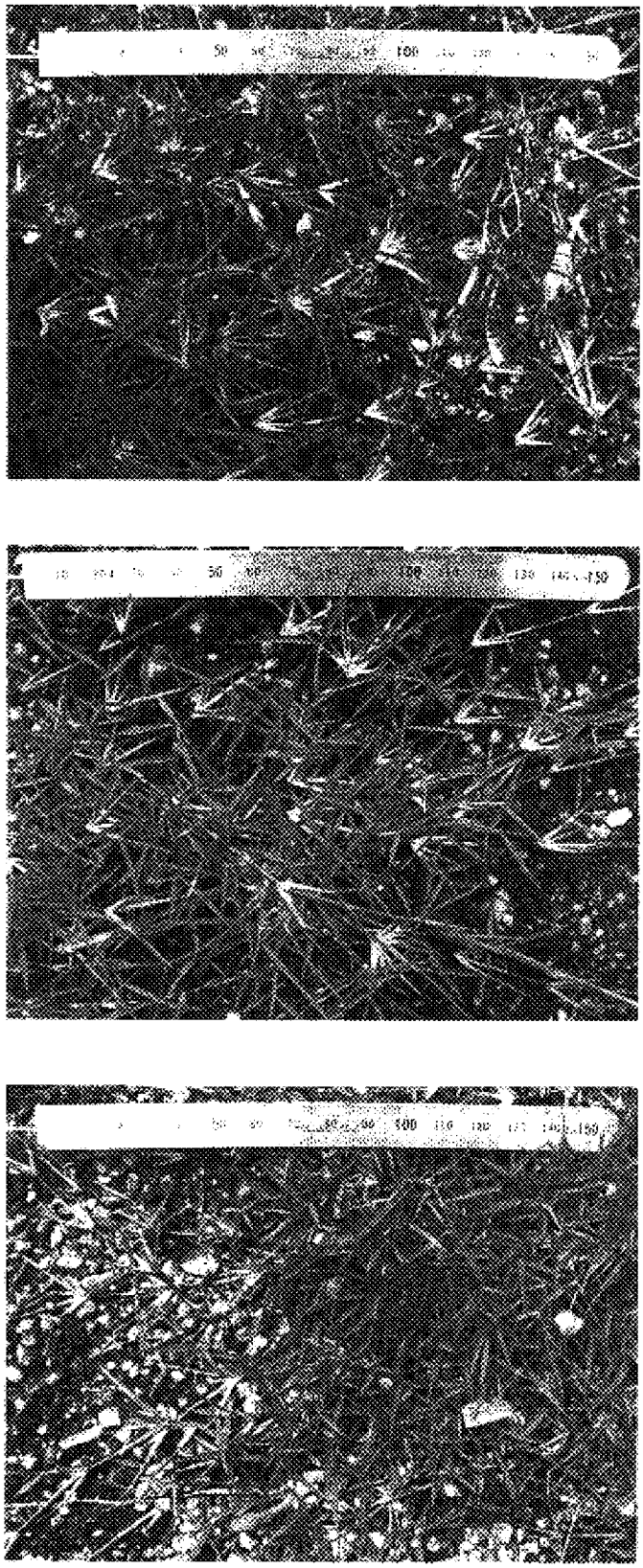

FIG. 4 is a set of photographs comparing stolons of control cultivars and the present cultivar (TM9) (Upper: Emerald; Middle: Winter Field; Lower: TM9). Photographed on Jul. 15, 2003 in Nishikamo-gun, Aichi, Japan.

Figure 5:
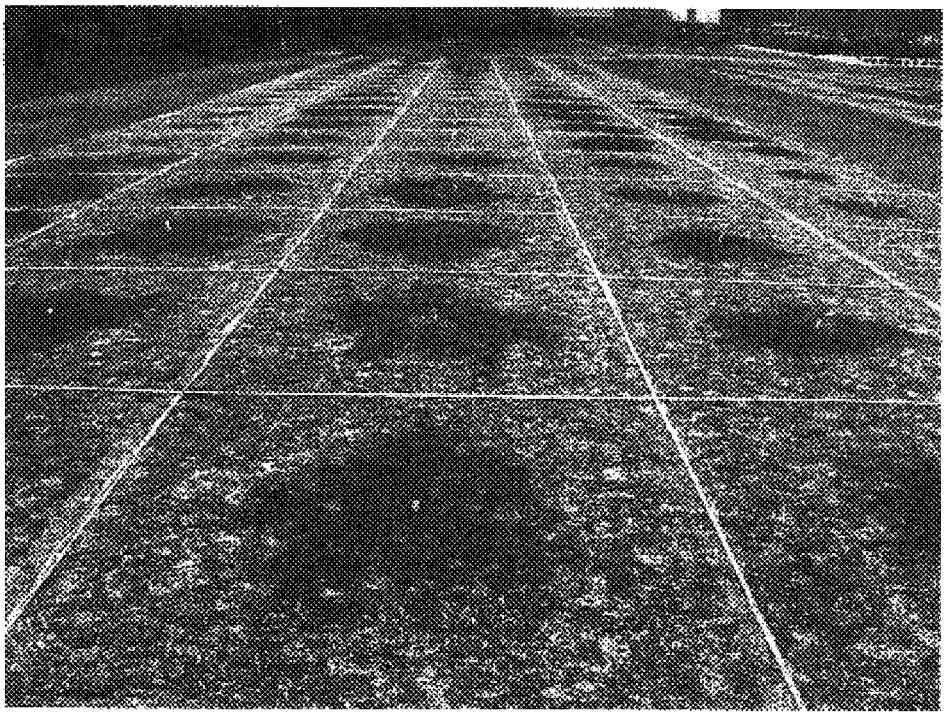
Figure 5:
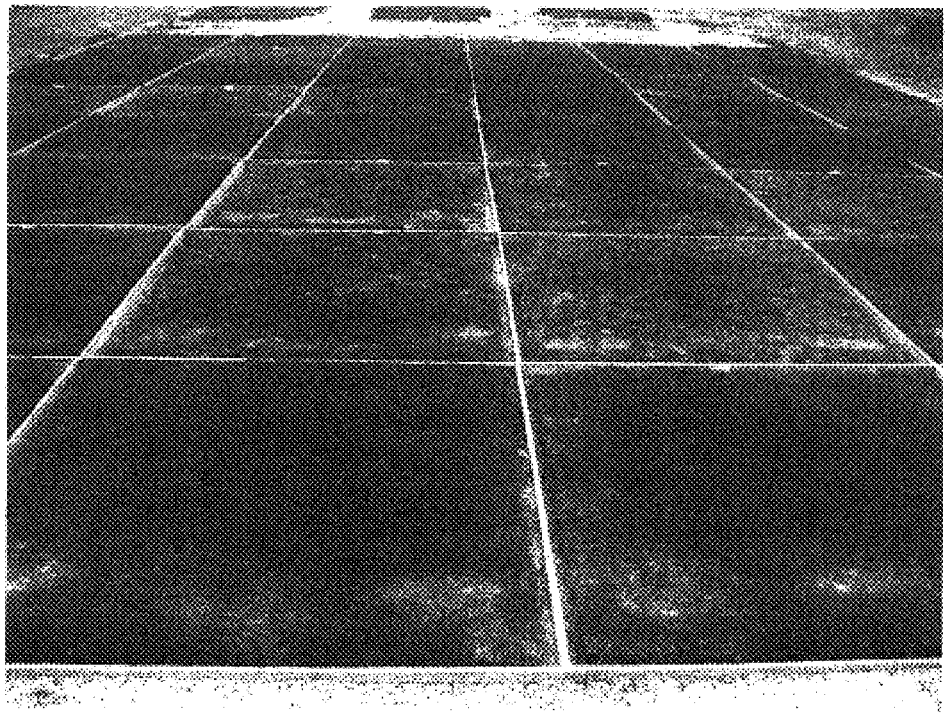

FIG. 5 is a set of photographs showing full views of test field for the present cultivar (TM9) (Upper: Individually planted plot; Lower: Densely plated plot). Photographed on Jul. 15, 2003 in Nishikamo-gun, Aichi, Japan.

DETAILED BOTANICAL DESCRIPTION OF THE PLANT

1. Characteristics of the plant body of the present invention:
1) Overview: Fifty thousand seeds of conventional Zoysiagrass cultivars (*Zoysia matrella* Merr.) were irradiated with soft X-ray (in the year 2000), 500 individuals exhibiting short plant height as a pot seedling were selected from the germinated individuals (in the year 2001), and 100 individuals were selected from among these seedlings based on their growing properties as a pot seedling. They were planted in a field and an outdoor cultivation test was initiated (in the year 2002). The present cultivar was obtained after completion of cultivation tests in various locations throughout Japan (completed in the year 2004). Characteristics of the present cultivar are as follows: creeping plant form; spikestem of medium-sized thickness and short length; extremely dense stolons of medium-sized thickness; leaves of very short length, narrow width and a thick color; a small number of spikelets; moderate initial growth; moderate plant vigor in spring and fall; medium (not early nor late) timing in spike-sprouting; spike-sprouting only in spring with a large number of spikes; medium (not early nor late) timing in turning green; medium (not early nor late) timing in turning red; good winter hardiness; good summer tolerance; medium shade tolerance; medium drought tolerance; medium salinity tolerance; medium tread pressure resistance.

2) Comparison with control cultivars (Table 1):

TABLE 1

| | | | Present cultivar |
|---|---|---|---|
| | Item | Trait | TM9 |
| 1 | Height | Mature plant height | Short (5.7 cm) |
| 2 | Plant | Plant | Creeping |
| 3 | Stem | Thickness of spikestem | Medium (0.9 mm) |
| | | Length of spikestem | Short (3 cm) |
| 4 | Stolon | Density of stolons | Extremely dense |
| | | Thickness of stolon | Medium (1.3 mm) |
| 5 | Foliage | Leaf length | Extremely short (3 cm) |
| | | Leaf width | Narrow (1.6 mm) |
| | | Leaf color | 137A green group |
| 6 | Spike | Spike length | Short (13 mm) |
| | | Spike color | 183A grayed purple group |
| | | Spikelet length | Medium (2.4 mm) |
| | | Spikelet width | Medium (1.0 mm) |
| | | Number of spikelet | Few (15) |
| 7 | Initial growth | Initial growth | Medium |
| 8 | Plant vigor | Plant vigor in spring | Moderate |
| | | Plant vigor in fall | Moderate |
| 9 | Spike-sprouting time | Beginning of spike-sprouting | Medium (not early nor late) |
| 10 | Spike-sprouting properties | Spike-sprouting in spring/fall | Spike-sprouting only in spring |
| | | Number of spikes | Many |
| 11 | Growing period | Timing to turn green | Medium (not early nor late) |
| | | Timing to turn red | Medium (not early nor late) |
| 12 | Winter hardiness | Good/Bad in winter hardiness | good |
| 13 | Summer tolerance | Good/Bad in summer tolerance | good |
| 14 | Environmental tolerance | Shade tolerance | Medium |
| | | Drought tolerance | Medium |
| | | Salinity tolerance | Medium |
| 15 | Tread pressure resistance | Tread pressure resistance | Medium |

TABLE 1-continued

| | | | Control cultivar | |
|---|---|---|---|---|
| | Item | Trait | Emerald | Winter Field |
| 1 | Height | Mature plant height | High (14.0 cm) | High (17.3 cm) |
| 2 | Plant | Plant | Intermediate | Intermediate |
| 3 | Stem | Thickness of spikestem | Medium (0.9 mm) | Medium (0.9 mm) |
| | | Length of spikestem | Short (3 cm) | Short (3 cm) |
| 4 | Stolon | Density of stolons | Medium to dense | Medium to dense |
| | | Thickness of stolon | Fine to Medium (1.1 mm) | Fine to Medium (1.0 mm) |
| 5 | Foliage | Leaf length | Short (6 mm) | Short to Medium (10 mm) |
| | | Leaf width | Narrow (1.7 mm) | Narrow (1.6 mm) |
| | | Leaf color | 144A yellow green group | 144A yellow green group |
| 6 | Spike | Spike length | Short (14 mm) | Short (12 mm) |
| | | Spike color | 183A grayed purple group | 183A grayed purple group |
| | | Spikelet length | Medium (2.5 mm) | Medium (2.5 mm) |
| | | Spikelet width | Medium (1.1 mm) | Medium (1.1 mm) |
| | | Number of spikelet | Few (16) | Few (15) |
| 7 | Initial growth | Initial growth | Medium | Medium |
| 8 | Plant vigor | Plant vigor in spring | Moderate | Moderate |
| | | Plant vigor in fall | Good | Good |
| 9 | Spike-sprouting time | Beginning of spike-sprouting | Medium (not early nor late) | Medium (not early nor late) |
| 10 | Spike-sprouting properties | Spike-sprouting in spring/fall | Spike-sprouting only in spring | Spike-sprouting only in spring |
| | | Number of spikes | Medium | Medium |
| 11 | Growing period | Timing to turn green | Medium (not early nor late) | Medium (not early nor late) |
| | | Timing to turn red | Medium (not early nor late) | Medium (not early nor late) |
| 12 | Winter hardiness | Good/Bad in winter hardiness | good | good |
| 13 | Summer tolerance | Good/Bad in summer tolerance | good | good |
| 14 | Environmental tolerance | Shade tolerance | Medium | Medium |
| | | Drought tolerance | Medium | Medium |
| | | Salinity tolerance | Medium | Medium |
| 15 | Tread pressure resistance | Tread pressure resistance | Medium | Medium |

*Notes:

*Type of plant: Lawn.*

*Name of the applied cultivar.*—TM9.

*Inventor.*—Kunio Matsui.

*Address of the assignee.*—1 Toyota-cho, Toyota-shi, Aichi, Japan.

*Cultivation site.*—Nishikamo-gun, Aichi, Japan (Latitude: N35°08'06", Longitude: E137°05'59").

*Place where characteristics research was conducted.*—Nishikamo-gun, Aichi, Japan (Latitude: N35°08'06", Longitude: E137°05'59").

*Name of researcher who conducted characteristics research.*—Kunio Matsui.

*Period when characteristics research was conducted.*—2002–2003.

*Control cultivar* (*most approximate cultivar*).—Emerald.

3) Characteristics by which the present cultivar is distinguished from the control cultivars:

a) Control cultivars: Emerald. Winter Field.

b) Distinguishing characteristics: The present cultivar can be distinguished from Emerald in that the present cultivar has a short height of 5.7 cm (whereas Emerald has a high height of 14.0 cm); a creeping plant form (whereas Emerald has an intermediate, i.e. semi-errect or semi-creeping plant form); extremely dense stolons (whereas Emerald has a medium to low stolon density); leaves of very short length of 3 cm (whereas Emerald has short leaves of 6 cm) and different color of 137A green group (whereas Emerald has 144A yellow green group) moderate plant vigor in fall (whereas Emerald has a good plant vigor); and a large number of spikes (whereas Emerald has a medium number of spikes).

The present cultivar can be distinguished from Winter Field in that the present cultivar has a short height of 5.7 cm (whereas Winter Field has a high height of 17.3 cm); a creeping plant form (whereas Winter Field has an intermediate, i.e., semi-erect or semi-creeping plant form); extremely dense stolons (whereas Winter Field has a medium to low stolon densisity); leaves of very short length of 3 cm, (whereas Winter Field has short leaves of 10 cm) and different color of 137A green group (whereas Emerald has 144A yellow green group); moderate plant vigor in fall (whereas Winter Field has a good plant vigor); and a large number of spikes (whereas Winter Field has a medium number of spikes).

4) Other information on the present cultivar:

*Susceptibility to the diseases and insects.*—TM9 had not shown any susceptibility in 20 months from April 2002 in Japan to the diseases and insects common to the Zoysiagrass genus.

*Internode length.*—19 mm.

*Internode diameter.*—1.3 mm.

*Leaf blade pubescence.*—Hairs absent on adaxial and abaxial leaf surface.

*Leaf ligule hairs.*—0.1 mm in length, continuously.

*Anthers color.*—183D grayed purple group.

*Stigmas color.*—8C reverse yellow group.

*Average number of floret per raceme.*—15.

*Culm total length including floral area to node below flag leaf.*—3.6 cm.

*Length of stem of inflorescence.*—2.3 cm.

*Floral area length.*—1.3 cm.

*Matured spikelet color.*—161D grayed yellow green group.

*Stolon color.*—60B red purple group and 144D yellow group.

5) Cultivation conditions for characteristic research experiment of above 1) to 4):

*a Cultivation site.*—Nishikamo-gun, Aichi, Japan (Latitude: N35°08'06", Longitude: E137°05'59").

*b Cultivation time and period.*—20 months from April, 2002.

*c Cultivation method* (*Examples.*—Cultivation style such as on bare ground, in a facility, field planting or pot planting, cultivation scale, etc.).

Pot seedlings reproduced by cutting of rhizomes and stolons and rooting them in soil were raised in greenhouse for two months and fix planted on bare ground in April along with control cultivars in order to perform a characteristic research experiment. Five individuals (triplicates) were fix planted at a density of one seedling per an area of 200 cm×200 cm in an individually planted plot while they were fix planted in triplicates at a density of one seedling per an area of 15 cm×15 cm in a dense plated test plot having an area of 150 cm×150 cm thereby performing a characteristic research experiment.

2. Reproduction method: Vegetative propagation; rhizomes, stolons, tillers and sod.

3. Conditions of keeping and storage the plant having identifiable characteristics:

*Place where the plant is maintained and/or stored.*—Nishikamo-gun, Aichi, Japan (Latitude: N35°08'06", Longitude: E137°05'59").

*Method of maintenance/storage.*—Pot planting and ground planting.

4. History of cultivating the present cultivar:

1) Material of new cultivar:

*Mother.*—*Zoysia matrella* Merr. (conventional cultivar cultivated in Ibaraki, Japan).

*Father.*—

*Family tree.*—

2) Cultivation site: Nishikamo-gun, Aichi, Japan (Latitude: N35°08'06", Longitude: E137°05'59").

3) History of cultivating the cultivar: Fifty thousand self-fertile seeds of conventional Zoysiagrass cultivars (raised in Ibaraki, Japan) were irradiated with soft X-ray in September, 2000, and individuals exhibiting short plant height as a pot seedling were selected from the germinated individuals. The thus selected lines were reproduced by root separation in May, 2001 and the uniformity of these vegetative propagated lines were respectively confirmed in greenhouse by February, 2002. Newly root separated lines were fix planted in a field in April, 2002. A line exhibiting a short leaf length and a satisfactory initial growth was selected and the stability thereof was confirmed to complete the cultivating of the new cultivar on Nov. 20, 2003.

5. Main use of the present cultivar: The present cultivar can be used for ground covering of a park, garden, etc.

6. Other items in relation to the cultivation of the present cultivar:

1) Applicable area: Warm area.

2) Specific cultivation site in Japan:

Address (zip code: 470-0201): 1099 Kurozasa-Marune, Miyoshi-cho, Nishikamo-gun, Aichi, Japan (Latitude: N35°08'06", Longitude: E137°05'59").

*Facility for travel.*—Meitetsu Toyoda line (Closest station: Miyoshigaoka).

3) Cultivation style: Normal cultivation. Bare ground.

Seasons suitable for seeding, planting, etc.:

*Other reproduction method.*—Vegetative propagation by stolons from the beginning of April to the beginning of May/year round.

Blooming season, harvest season, and any other seasons in cultivation stage suitable for specifying characteristics of the present cultivar:

*Blooming season.*—From the beginning to the end of May/year round.

*Greening season.*—From the end of April to the end of October/year round.

4) Other items to be mentioned for the cultivation of the present cultivar: The present cultivar is creeping in plant form and short in leaf length, which allows weeds readily to grow. Frequent weeding is therefore required.

5) Information about the cultivation technique and raising condition of the present cultivar is available from the below:

Address (zip code: 470-0201): 1099 Kurozasa-Marune, Miyoshi-cho, Nishikamo-gun, Aichi, Japan (Latitude: N35°08'06", Longitude: E137°05'59").

*Name.*—Kunio Matsui (TEL 81-0561-36-8441).

7. Other information: When the present cultivar is allowed freely to grow, the plant height (i.e. the height from the ground to the tip of the leaf blade) is as about half as that of Emerald.

What is claimed is:

1. A new and distinct variety of *Zoysia matrella* Merr. plant named TM9 illustrated and described in the present invention.

* * * * *